US012041939B2

(12) United States Patent
Webb et al.

(10) Patent No.: US 12,041,939 B2
(45) Date of Patent: Jul. 23, 2024

(54) ENZYME-LOADED POLLEN-MIMICKING MICROPARTICLES FOR ORGANOPHOSPHATE DETOXIFICATION OF INSECT POLLINATORS

(71) Applicant: CORNELL UNIVERSITY, Ithaca, NY (US)

(72) Inventors: James Webb, Ithaca, NY (US); Jing Chen, Ithaca, NY (US); Minglin Ma, Ithaca, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 17/544,375

(22) Filed: Dec. 7, 2021

(65) Prior Publication Data

US 2022/0174962 A1 Jun. 9, 2022

Related U.S. Application Data

(60) Provisional application No. 63/122,692, filed on Dec. 8, 2020.

(51) Int. Cl.

| | |
|---|---|
| ***A01N 63/50*** | (2020.01) |
| ***A01N 25/04*** | (2006.01) |
| ***A01N 25/08*** | (2006.01) |

(52) U.S. Cl.

CPC ............. *A01N 63/50* (2020.01); *A01N 25/04* (2013.01); *A01N 25/08* (2013.01)

(58) Field of Classification Search

CPC ...................................................... A01N 63/50

See application file for complete search history.

(56) References Cited

U.S. PATENT DOCUMENTS

| | | | |
|---|---|---|---|
| 6,541,230 B1 | 4/2003 | Gordon et al. | |
| 7,348,169 B1 | 3/2008 | Singh et al. | |
| 9,976,130 B1 | 5/2018 | Guelta et al. | |
| 10,808,238 B2 | 10/2020 | Walker et al. | |
| 2002/0050659 A1 | 5/2002 | Toreki et al. | |
| 2003/0124167 A1 | 7/2003 | Thies | |
| 2004/0161818 A1 | 8/2004 | Horne et al. | |
| 2009/0218543 A1 | 9/2009 | Hatton et al. | |
| 2010/0248334 A1 | 9/2010 | McDaniel | |
| 2013/0302392 A1 | 11/2013 | Mistry et al. | |
| 2013/0337066 A1 | 12/2013 | Zhang et al. | |
| 2015/0191607 A1 | 7/2015 | McDaniel | |
| 2016/0050914 A1 | 2/2016 | Markus et al. | |
| 2016/0222372 A1 | 8/2016 | Walper et al. | |
| 2016/0355792 A1* | 12/2016 | Pegan ................ | A61K 31/5513 |
| 2017/0245493 A1 | 8/2017 | Gezundhait et al. | |
| 2020/0054006 A1 | 2/2020 | Schwantes | |
| 2021/0237020 A1 | 8/2021 | Bachawala et al. | |
| 2021/0290539 A1 | 9/2021 | Gourdie et al. | |

FOREIGN PATENT DOCUMENTS

| | | |
|---|---|---|
| WO | 2004064997 A1 | 8/2004 |
| WO | 2016176041 A1 | 11/2016 |

OTHER PUBLICATIONS https://futureyouhealth.com/ingredient-definitions-list#:~:text=Calcium%20Carbonate%20%2D%20A%20common%20bulking,of%20calcium%2C%20an%20essential%20mineral. (Year: 2016).*
Wayback Machine for Futureyouhealth.com (Year: 2016).*
De Jong et al. (Drug delivery and nanoparticles: Applications and hazards, Int J Nanomedicine, 2008) (Year: 2008).*
https://tereos.com/en/activities-and-products/markets/pharmaceuticals-and-cosmetics/ (Year: 2019).*
Wayback Machine for tereos.com (Year: 2019).*
Cai et al. (Porous microsphere and its applications, Int J Nanomedicine, 2013). (Year: 2013).*
Chen, J., et al., "Pollen inspired enzymatic microparticles to reduce organophosphate toxicity in managed pollinators", Nature Food, May 2021, pp. 339-347, vol. 2.
Liu, W.-L., et al., "Recent Advances of Cell Membrane-Coated Nanomaterials for Biomedical Applications", Advanced Functional Materials 2020, Revised May 18, 2020, pp. 1-23, 2003559.
Pang, Z., et al., "Detoxification of Organophosphate Poisoning Using Nanoparticle Bioscavengers", ACS 2015, Received for review Apr. 9, 2015, accepted May 30, 2015, Published online Jun. 8, 2015, pp. 6450-6458, vol. 9, No. 6.
Thankur, "Enzymatic Bioremediation of Organophosphate Compounds-Progress and Remaining Challenges", Frontiers in Bioengineering and Biotechnology, Accepted Oct. 9, 2019, Published Nov. 8, 2019, Nov. 1, 2019, pp. 1-21, vol. 7, Article 289.

(Continued)

*Primary Examiner* — Andrew S Rosenthal
*Assistant Examiner* — Danielle Kim
(74) *Attorney, Agent, or Firm* — Scully, Scott, Murphy & Presser, P.C.

(57) ABSTRACT

A composition for detoxifying insect pollinators from one or more organophosphate pesticides, the composition containing microparticles comprising: (i) a phosphotriesterase; (ii) nanoparticles; and (iii) a surface active agent. Also disclosed herein is an aqueous suspension comprising the above-described detoxifying microparticles in an external aqueous medium, which may also contain an insect pollinator attractant. Also described herein is a method for detoxifying insect pollinators of one or more organophosphate pesticides, the method comprising placing the detoxifying aqueous suspension in a location accessible to the insect pollinators to permit the insect pollinators to ingest the detoxifying aqueous suspension, wherein the detoxifying aqueous suspension comprises microparticles, as described above, suspended in an external aqueous medium, typically also including an insect pollinator attractant in the external aqueous medium.

39 Claims, 15 Drawing Sheets
(14 of 15 Drawing Sheet(s) Filed in Color)

(56) References Cited

OTHER PUBLICATIONS

Webb, J.E.L., "Hosphotriesterase Loaded Microparticles to Control Organophosphate Toxicity in Pollinators", A Thesis Presented to the Faculty of the Graduate School of Cornell University In Partial Fulfillment of the Requirements for the Degree of Master of Science, Aug. 2020, 44 pages.
Wei, W., et al., "Construction of Robust Enzyme Nanocapsules for Effective Organophosphate Decontamination, Detoxification, and Protection", Advanced Materials 2013, Published online Feb. 25, 2013, pp. 2212-2218, 25.

* cited by examiner

ENZYME-LOADED POLLEN-MIMICKING MICROPARTICLES FOR ORGANOPHOSPHATE DETOXIFICATION OF INSECT POLLINATORS

CROSS REFERENCE TO RELATED APPLICATIONS

This application claims the benefit of priority from U.S. Provisional Application No. 63/122,692, filed on Dec. 8, 2020, which is herein incorporated by reference in its entirety.

GOVERNMENT SUPPORT

This invention was made with government support under grant number 2017-18-107 awarded by the National Institute of Food and Agriculture, US Department of Agriculture, Hatch, and under Award Number R21-NS10383-01 awarded by the Counter ACT Program of the National Institute of Health, and under Award Number IIP-1918981 awarded by the National Science Foundation. The government has certain rights in the invention.

FIELD OF THE INVENTION

The present invention generally relates to methods for detoxifying or preventing toxification of insect pollinators, such as bees. The present invention more particularly relates to detoxifying or preventing toxification of insect pollinators by feeding the insect pollinators a composition that degrades or removes a toxifying compound, such as a pesticide toxic to the insect pollinators.

BACKGROUND OF THE INVENTION

One-third of U.S. crops are dependent on managed and native bees for sustained production, yield, and quality. Pollinators contribute $24 billion to the U.S. economy, of which honeybees are responsible for over $15 billion (The White House Archives, 2014, Fact Sheet: *The Economic Challenge Posed By Declining Pollinator Populations*, Washington D.C.: Office of the Press Secretary). However, bee populations are rapidly declining (Kulhanek, K., et al., *Journal Of Apicultural Research,* 56(4), 328-340, 2017. https://doi.org/10.1080/00218839.2017.1344496). Beekeepers lose on average one-third of colonies each winter and more than 700 U.S. native bee species are now at risk of extinction (The Center for Biological Diversity, 2017. *Pollinators In Peril.* Portland Oregon). Between 2013-2019, the U.S. beekeeping industry spent $2 billion, a third of its income, on replacing 10 million hives (Amadeo, K. (2019). Bee Colony Collapse Disorder and Its Impact on the Economy. The Balance). The loss of managed colonies has caused a rise in pollination fees for many crop farmers. Growers are currently facing diminished crop yields as a result of poor pollination from weakened colonies.

The application of insecticides, and other agrochemicals is considered to be a major cause of managed and native bee population loss (D. Goulson et al., *Science,* 347, 10, 2015). Insecticides can have lethal and sub-lethal effects on pollinators, both at an individual and colony level, often through the impairment of vital neuronal pathways (J. Yao et al., *Journal of Economic Entomology,* 111, 4, August 2018, 1517-1525). Other agrochemicals, such as fungicides, can cause synergistic effects with other toxins by destroying beneficial gut bacteria, which are essential for defending against viruses, parasites and insecticides (A. Iverson et al., *Apidologie,* 50, 733-744, 2019). In the case of social bees, chemicals can be transported back into the hive within pollen and nectar and accumulate within wax, developing brood and other bee castes (S. McArt et al., *Sci. Rep.,* 7, 46554, 2017). Research has shown over the course of a year up to 93 different foreign compounds accumulated within a colony and that the number of pesticides was a strong predictor of colony death (K. Traynor et al., *Sci. Rep.,* 6, 33207, 2016).

Organophosphate (OP) pesticides, in particular, are heavily relied upon in agricultural production to prevent crop loss due to numerous types of insects. OPs have a market of over $7 billion and account for more than a third of insecticide sales worldwide and often lead to pollinator exposures and exhibit high toxicity towards honey bees and bumble bees (S. R. Rissato et al., Food Chem., 101, 1719-1726, 2007). OP insecticides influence insect cholinergic neural signaling through inhibition of carboxyl ester hydrolases, particularly acetylcholinesterase (AChE) which breaks down acetylcholine. OPs inactivate AChE through irreversible covalent inhibition, causing a build-up of acetylcholine and overstimulation of nicotinic and muscarinic receptors (J. V. Peter et al., *Indian J. Crit. Care Med.,* 18, 735, 2014).

Some examples of organophosphate pesticides include malathion, parathion, methyl parathion, chlorpyrifos, diazinon, dichlorvos, phosmet, fenitrothion, tetrachlorvinphos, azamethiphos, azinphos-methyl, azinphos-ethyl, and terbufos. Malathion and parathion are the two of the most widely applied OPs in commercially pollinated crops. Malaoxon, malathion's metabolite, is 1000-fold stronger at inhibiting AChE than malathion (0. P. Rodriguez et al., *Bull. Environ. Contam. Toxicol.,* 58, 171-176, 1997). Malathion and parathion exhibit oral $LD_{50}$'s of 0.38 and 0.175 μg/bee respectively (C. D. S. Tomlin, The Insecticide Manual: A World Compendium, British Crop Production Council, ISBN 9781901396188, 2009).

Although these pesticides are useful in mitigating the damage caused by agricultural pests, they unfortunately also have an adverse effect on insect pollinators, such as bees (e.g., honey bees and bumble bees), as discussed above. As insect pollinators are critical for agriculture and farming, the use of such pesticides can result in a critical decline in pollination, which represents a threat to global food production and ecological balance.

SUMMARY OF THE INVENTION

The present invention provides a downstream solution to the persistent and pernicious problem of inadvertent pesticide toxification of insect pollinators, particularly bees. To achieve the solution, a method is herein described for detoxifying insect pollinators that have ingested one or more organophosphate pesticides. The method more particularly involves feeding a detoxifying formulation to a community of insect pollinators, wherein the detoxifying formulation includes microparticles containing: i) a phosphotriesterase; (ii) nanoparticles; and (iii) a surface active agent. The phosphotriesterase functions to hydrolyze the organophosphate pesticide inside the insect pollinator when ingested by the insect pollinator. The nanoparticles may have an inorganic composition (e.g., a carbonate) or organic composition (e.g., a biodegradable polyester). In some embodiments, the phosphotriesterase is dissolved or suspended in an aqueous medium (i.e., internal aqueous medium) contained within each microparticle.

Typically, the microparticles are provided to the insect pollinators in the form of a suspension of the microparticles in an external aqueous medium, typically with an insect pollinator attractant included in the external aqueous medium. The method is typically practiced by placing the detoxifying composition, typically as an aqueous suspension, in a location accessible to the insect pollinators to permit the insect pollinators to ingest the detoxifying composition.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 2A (panels left, middle, and right) provides microscopic images of unmodified $CaCO_3$ microparticles (control) in pH 7.4 (left panel) and PIMs in pH 7.4 (middle panel) and pH of 4.8 (right panel). Note: CMP denotes unmodified $CaCO_3$ microparticles, included as the control. Insets are higher magnifications. FIG. 2B plots size distribution of PIMs and unmodified microparticles in pH 7.4 and PIMs in pH 7.4 and 4.8. FIG. 2C plots relative suspension stability of unmodified microparticles and PIMs in 2 g $ml^{-1}$ sucrose. FIG. 2D shows sucrose solution (left panel) and large scale PIM suspension (right panel). FIG. 2E provides morphological analysis and size distribution analysis of PIMs fabricated at a large scale. FIG. 2F (panels left, middle, and right) shows SEM images of microparticles at different magnifications (as indicated) to determine PIM surface morphology. FIG. 2G shows pore size distribution analysis of PIMs and PIMs loaded with HSA. The data are presented as means, and error bars represent the standard deviation.

FIG. 3A shows fluorescent imaging of PIMs containing Cy5.5-modified gelatin (middle panel), FITC-conjugated HAS (left panel), and a merge image (right panel). FIG. 3B shows protein loading efficiency (PLE) of CMP and PIM loaded with HSA at 5, 10 and 15% PFC. FIG. 3C shows PLE of PIM loaded with OPT at 2% and 5% PFC. FIG. 3D shows relative activity of OPT-PIM and free OPT in paraoxon hydrolysis under pH 7.4 and 4.8 (n=3). FIG. 3E shows relative activity of OPT-PIM and free OPT in malathion hydrolysis under pH 7.4 and 4.8 (n=3). FIG. 3F shows temperature-dependent relative activity of OPT-PIM and free OPT in paraoxon hydrolysis when incubated at temperatures 30, 40, 50 and 60° C. (n=3). FIG. 3G shows long-term relative activity of OPT-PIM and free OPT in paraoxon hydrolysis when stored at room temperature and 4° C. (n=3). Statistical analysis was performed by using one-way ANOVA tests (FIGS. 3D and 3E) and two-way ANOVA tests (FIGS. 3F and 3G). Data are presented as means and error bars represent the standard deviation. NS, no statistical significance; room temperature (r.t.).

FIG. 4A shows GI tracts following HSA-PIM treatment; fluorescence was maintained up to 12 h post-consumption. Microparticle morphology was clearly visible and microparticles were successfully drawn into the midgut (n=3; relatively brighter background at 1 and 12 h was probably due to protein leakage during digestion). FIG. 4B shows GI tracts following free-HSA treatment (n=3).

FIG. 5A is a schematic showing that formation of thiocholine from acetylthiocholine through AChE cleavage can be characterized using 5,5'-dithiobis-2-nitrobenzoic acid (DTNB). DTNB and thiocholine react to form $TNB^{2-}$, the absorbance of which can be measured at 412 nm. FIG. 5B shows relative activity of AChE from homogenized honeybees when incubated in 0.5 mM paraoxon or DI water (the positive control) and treated with samples of free OPT, OPT-PIM and DI water (the negative control). For this experiment, n=9. The positive control is homogenized honeybee cells without any paraoxon treatment; the negative control is homogenized honeybee cells treated with paraoxon but no free OPT or OPT-PIMs treatment. FIG. 5C depicts an exemplary apparatus for determining mortality following contaminated pollen ball consumption against PIM treatment in syrup. FIG. 5D shows the survival rate of bumblebees following acute exposure to paraoxon (50 μg $g^{-1}$ pollen) over 12 hours when treated with 500 μg $ml^{-1}$ OPT treatments (n=40). FIG. 5E is a plot of exposure to paraoxon (15 μg $g^{-1}$ pollen) over 10 days (n=50). FIG. 5F is a plot of exposure to malathion (750 μg $g^{-1}$ pollen) over 10 days (n=50). Statistical analysis was performed by using one-way ANOVA tests (FIGS. 5B and 5D). Data are presented as means and error bars represent the standard deviation.

DETAILED DESCRIPTION OF THE INVENTION

Figure 1:
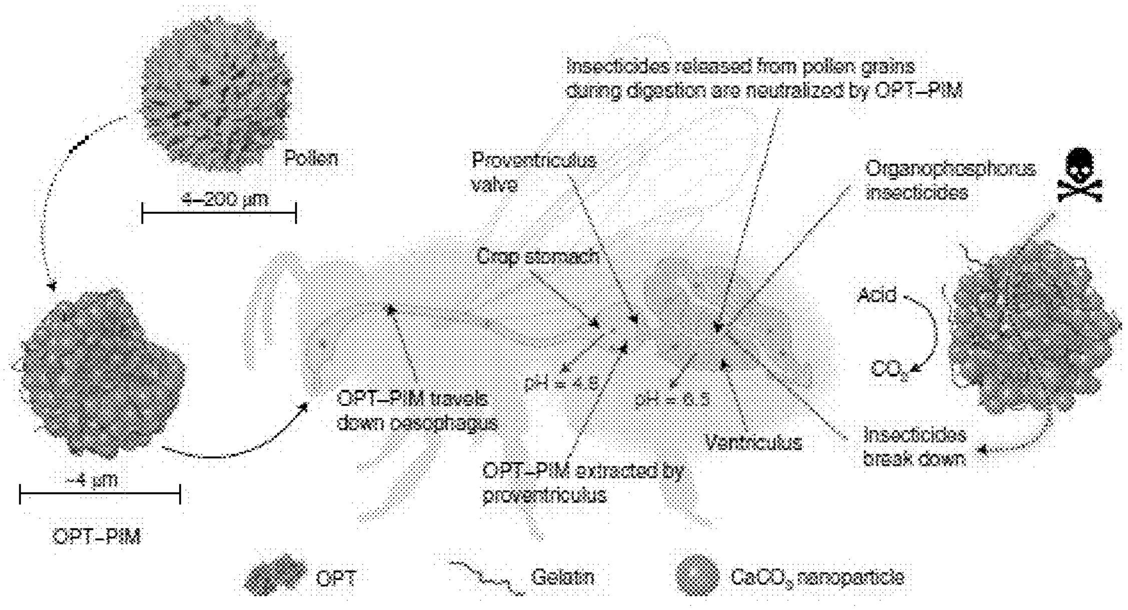
FIG. 1. A schematic of the passage of microparticles through a bee digestive tract. Microparticles analogous to pollen grains move into the midgut as they are extracted by the proventriculus, which draws particulates out of the crop stomach. The PIM structure protects the encapsulated protein from gastric acidity. PIMs are retained in the midgut to detoxify pesticides as they are released during pollen digestion.

In one aspect, the present disclosure is directed to a composition for detoxifying insect pollinators that have ingested or otherwise internalized one or more organophosphate (OP) compounds or substances, typically used as pesticides. The term "pesticide," as used herein, broadly includes any substance applied onto plants to improve the quality, growth, or product yield of the plants. The pesticide generally possesses one or more properties of controlling or regulating agricultural or horticultural pests, wherein the pests may be crop-damaging insects, animals, fungi, or undesired plant life (e.g., invasive species or weeds). As noted earlier above, although pesticides are used for controlling or killing crop-damaging insects, agricultural pesticides are generally not intended for controlling or killing insect pollinators. The pesticide may be, more specifically, an insecticide, herbicide, fungicide, or nematicide. For purposes of the present disclosure, the pesticide is an organophosphate compound or substance. Some examples of organophosphate pesticides include malathion, parathion, methyl parathion, chlorpyrifos, diazinon, dichlorvos, phosmet, fenitrothion, tetrachlorvinphos, azamethiphos, azinphos-methyl, azinphos-ethyl, and terbufos.

A first component (component i) of the detoxifying composition is a phosphotriesterase. The phosphotriesterase, also known as an aryldialkylphosphatase or organophosphate hydrolase, may be any of the types (variants or strains) known and may be derived from any bacterial source. Phosphotriesterases are metalloenzymes that hydrolyze the triester linkage found in OP insecticides (A. B. Pinjari et al.,

*Lett. Appl. Microbiol.,* 57, 63-68, 2013). There are several variants of phosphotriesterase; the most frequently used, amidohydrolase phosphotriesterase (OPT), is isolated from bacteria *P. diminuta* or *Flavobacterium* ATCC 27551 and exhibits a TIM-barrel fold structure (Y. Zheng et al., *Appl. Biochem. Biotechnol.,* 136, 233-241, 2007). OPT can be produced from transfected *E. coli* culture with the appropriate OPT plasmid sequence (C. Roodveldt et al., *Protein Eng. Des. Sel.,* 18, 51-58, 2005). OPT has a wide substrate specificity; it exhibits optimal hydrolysis upon encountering paraoxon (parathion's metabolite), at a rate approaching the limit of diffusion (S. R. Caldwell et al., *Biochemistry,* 30, 7438-7444, 1991). OPT performs best hydrolyzing substrates which possess phenol leaving groups, yet it will also successfully degrade thiol linkages as in the case of malathion (S. B. Hong et al., *Biochemistry,* 35, 10904-10912, 1996). Notably, OPT application has demonstrated poor efficacy in industry due to its poor stability at a low pH and high temperatures (C. Y. Yang et al., *ChemBioChem,* 15, 1761-1764, 2014). Bioactivity rapidly declines at pHs less than 8.0. At pH of 7.0, activity is less than half of its maximum potential. At the optimum pH range of 8.0-9.5, the $Co^{2+}$ OPT complex maintains thermostability at less than 45° C., above which, the stability rapidly declines until deactivation at 60° C. (D. Rochu et al., *Biochem. J.* 380, 627-633, 2004).

A second component (component ii) of the detoxifying composition is nanoparticles. The nanoparticles can have any solid composition, provided that the solid composition is non-toxic to insect pollinators. The nanoparticles should also have a composition that is substantially insoluble in water or aqueous solution and also non-reactive with water. The nanoparticles can have a particle size of, for example, 1, 2, 5, 10, 20, 30, 40, 50, 100, 200, 250, 300, 350, 400, 450, or 500 nm, or a particle size within a range bounded by any two of the foregoing values, e.g., 1-500 nm, 1-200 nm, 1-100 nm, or 1-50 nm. In some embodiments, any range of nanoparticle sizes derivable from the above values may be excluded.

In a first set of embodiments, the nanoparticles have an inorganic composition. The inorganic composition may be a non-toxic salt, such as a carbonate or sulfate salt, or combination thereof. Some examples of carbonate salts include sodium carbonate, potassium carbonate, calcium carbonate, and magnesium carbonate. Some examples of sulfate salts include sodium sulfate, potassium sulfate, calcium sulfate, and magnesium sulfate. The carbonate composition may or may not contain a portion thereof in sulfate form, typically no more than 20 wt % of the carbonate composition. The inorganic composition may alternatively be a metal oxide or metal sulfide composition, wherein the "metal" refers to any element substantially non-toxic to insect pollinators. The metal may be, for example, an alkaline earth element, transition metal element, or main group element. Some examples of metal oxide compositions include silicon oxide (silica), aluminum oxide (alumina), zinc oxide, magnesium oxide, calcium oxide, titanium oxide, yttrium oxide (yttria), and zirconium oxide. Analogous metal sulfide compositions can be derived by replacing oxide with sulfide in any of the foregoing examples.

In a second set of embodiments, the nanoparticles have an organic composition. The organic composition may be a polymer composition. Some examples of organic polymeric compositions include polyethylene, polypropylene, polyethylene terephthalate, polyurethanes, polyamides, polycarbonates, polyureas, vinyl addition polymers (e.g., polyacrylate, polymethylacrylate, polymethacrylate, polymethylmethacrylate, polyvinylalcohol, and polyvinylacetate) and biodegradable ester polymeric compositions, such as polylactic acid (PLA) and polyglycolic acid (PGA).

In some embodiments, the nanoparticles may have an acid-scavenging composition, with carbonate compositions being exemplary. The acid-scavenging composition may be inorganic or organic and should be capable of neutralizing an acid and/or maintaining an alkaline condition in an aqueous medium in contact with the acid-scavenging composition.

A third component (component iii) of the detoxifying composition is a surface active agent. The surface active agent should be non-toxic to insect pollinators. The surface active agent may be any substance known in the art to have a surface active property, i.e., surfactant ability, including any of the non-toxic surfactants known in the art. The surface active agent may be, for example, a natural or synthetic polymer. In some embodiments, the surface active agent is a natural-based surfactant, such as a polypeptide (e.g., protein) or polysaccharide (sugar or carbohydrate). Some examples of polypeptide surface active agents include gelatin, collagen, fibrin, polylysine, and polyaspartate. Some examples of polysaccharide surface active agents include dextran, dextrose, starch, maltodextrin, chitosan, pectin, agarose, hemicellulose (e.g., xylan), alginate, carrageenan, guar gum, xanthan gum, locust bean gum, and cellulose gum. The surface active agent may alternatively be amphiphilic by containing one or more hydrophilic portions and one or more hydrophobic sections. Some examples of amphiphilic surface active agents include sodium lauryl sulfate, alkylbenzene sulfonates, and lignin sulfonates. Some examples of synthetic polymers include polyvinyl alcohol, polyvinyl acetate, and polysorbate-type non-ionic surfactants (e.g., polysorbate 80).

The surface active agent may alternatively be a non-ionic surfactant, which typically contains at least one polyalkylene oxide (hydrophilic) portion attached to a hydrophobic hydrocarbon portion. The polyalkylene oxide (PAO) portion is typically polyethylene oxide (PEO), although polypropylene oxide (PPO), and polybutylene oxide (PBO) may also serve as the PAO. The PAO typically includes at least or greater than 5, 10, 15, 20, 30, 40, or 50 alkylene oxide units. As part of the hydrophilic portion, the non-ionic surfactant may alternatively or in addition include one or more hydroxy (OH) or cyclic ether (e.g., tetrahydrofuran) groups per molecule. The hydrocarbon portion is generally constructed solely of carbon and hydrogen atoms, except that one or more fluorine atoms may or may not be present. The hydrocarbon portion may be or include one or more alkyl groups, alkenyl groups, cycloalkyl groups, and aromatic groups (e.g., phenyl). In some embodiments, the non-ionic surfactant includes a hydrocarbon group corresponding to a linear or branched hexyl, heptyl, octyl, nonyl, decyl, undecyl, or dodecyl group. Some examples of non-ionic surfactants include: (i) Triton® X-100 and Igepal® surfactants, which contain a (1,1,3,3-tetramethylbutyl)phenyl portion; (ii) polysorbate (Tween®) surfactants, such as polysorbate 80, which contain a polyethoxylated sorbitan moiety attached (typically via an ester bond) to a hydrocarbon group, such as an undecyl group; (iii) non-ionic triblock copolymers, also known as poloxamers, such as Pluronic® surfactants, which typically contain alternating PEO and PPO units, such as PEO—PPO-PEO and PPO-PEO-PPO surfactants; and (iv) Brij® surfactants, which contain a PEO portion attached to an alkyl portion (typically 12-20 carbon atoms).

The above described components (i)-(iii) are included as components of microparticles. The end result is that the microparticles are composed of at least or solely components (i)-(iii). In some embodiments, the phosphotriesterase and surface active agent are dispersed throughout each microparticle. In other embodiments, the phosphotriesterase is contained within a core portion of the microparticle, with the nanoparticles forming a shell surrounding (encapsulating) the phosphotriesterase core. The surface active agent may be in the core, shell, or both. The encapsulation of the phosphotriesterase provides the advantage of protecting the phosphotriesterase from unfavorable acidic GI conditions within the insect pollinator. In further embodiments, the phosphotriesterase may be dissolved or suspended in an aqueous medium within each microparticle. The aqueous medium can have any suitable pH, particularly an alkaline pH, such as a pH of at least or greater than 7, 7.5, 8, 8.5, 9, 9.5, or 10, or a pH within a range bounded by any two of the foregoing values.

The microparticles may or may not include one or more additional components. In one embodiment, the microparticles further include an insect pollinator attractant admixed with components (i), (ii), and/or (iii). In another embodiment, the microparticles further include pollen admixed with components (i), (ii), and/or (iii). In another embodiment, the microparticles further include one or more nutrients for insect pollinators. The one or more nutrients may be, for example, one or more carbohydrates (e.g., sugar or nectar), amino acids, vitamins, minerals, or lipids (e.g., fatty acids or sterols).

The microparticles typically have a size of at least 0.1 microns and up to 200 microns. In different embodiments, the microparticles have a size of precisely, about, at least, up to, or less than 0.1, 0.2, 0.5, 1, 2, 5, 10, 20, 30, 40, 50, 100, 150, or 200 microns, or a size within a range bounded by any two of the foregoing values (e.g., 0.1-200 microns, 0.1-150 microns, 0.1-100 microns, 0.1-50 microns, 1-200 microns, 1-150 microns, 1-100 microns, 1-50 microns, 10-200 microns, 10-150 microns, 10-100 microns, or 10-50 microns). In some embodiments, any range of microparticle sizes derivable from the above values may be excluded.

The microparticles may also possess an outer surface porosity, with the pores typically being nanosized, such as 1-500 nm or 1-100 nm in size. Typically, the pores correspond to interstitial spaces between the nanoparticles. In different embodiments, the pores have a size of precisely, about, at least, greater than, up to, or less than, for example, 1, 2, 5, 10, 20, 50, 100, 150, 200, 250, 300, 350, 400, 450, or 500 nm, or a pore size within a range bounded by any two of the foregoing values.

In another aspect, the present disclosure is directed to a detoxifying aqueous suspension containing any of the detoxifying microparticles described above suspended in an external aqueous medium. The external aqueous medium can have any suitable pH, particularly an alkaline pH, such as a pH of at least or greater than 7, 7.5, 8, 8.5, 9, 9.5, or 10, or a pH within a range bounded by any two of the foregoing values. At least when being used to administer to insect pollinators, the detoxifying aqueous suspension typically contains an insect pollinator attractant in the external aqueous medium, the detoxifying microparticles, or both. The insect pollinator attractant may be or include, for example, sucrose, a plant extract, fruit extract, or a pheromone. The attractant may be present in an amount of, for example, 1-5 g/mL in the external aqueous medium. However, in some embodiments, an attractant is not included. In some embodiments, the external aqueous medium includes a surface active agent to help stabilize the suspension. The external aqueous medium may also include one or more auxiliary agents, such as, for example, a buffer, anti-bacterial agent, or nutrient appropriate for insect pollinators. In some embodiments, the suspended microparticles are mixed with pollen to form a macroscopic pollen ball, which is then administered to the insect pollinators in the same manner described above, such as in the form of an aqueous suspension.

In another aspect, the present disclosure is directed to a method for using the detoxifying composition to protect insect pollinators from the harmful effects of organophosphate pesticides. The insect pollinators typically belong to the order Hymenoptera, such as bees (e.g., honey bees or bumble bees) or wasps. In the method, the detoxifying composition in the form of microparticles or suspension thereof, as described above, is placed in a location accessible to the insect pollinators to permit the insect pollinators to ingest the detoxifying composition. Upon ingestion, the phosphotriesterase functions to hydrolyze the organophosphate pesticide inside the insect pollinator. In some embodiments, the method results in at least or above 50%, 60%, 70%, 80%, or 90% survival of the insect pollinators compared to insect pollinators administered an external aqueous medium without the detoxifying microparticles.

Typically, the microparticles are provided to the insect pollinators in the form of a suspension of the microparticles in an external aqueous medium, as described above, typically with an insect pollinator attractant included in the external aqueous medium. The attractant may be present in the external aqueous medium in an amount of, for example, 1-5 g/mL in the external aqueous medium. The insect pollinator attractant may be or include, for example, sucrose, a plant extract, fruit extract, or a pheromone. The method is typically practiced by placing the detoxifying aqueous suspension in a location accessible to the insect pollinators to permit the insect pollinators to ingest the detoxifying aqueous suspension.

Examples have been set forth below for the purpose of illustration and to describe the best mode of the invention at the present time. However, the scope of this invention is not to be in any way limited by the examples set forth herein.

EXAMPLES

Overview

The following experiments describe a low-cost, scalable in vivo detoxification strategy for removing organophosphate insecticides from insect pollinators. The method involves encapsulation of phosphotriesterase (OPT) in pollen-inspired microparticles (PIMs). Uniform and consumable PIMs were developed with capability of loading OPT at 90% efficiency and protecting OPT from degradation in the pH of a bee gut. Microcolonies of *Bombus impatiens* fed malathion-contaminated pollen patties demonstrated 100% survival when fed OPT-PIMs but 0% survival with OPT alone, or with plain sucrose within five and four days, respectively. Thus, the detrimental effects of malathion were eliminated when bees consumed OPT-PIMs. This design presents a versatile treatment that can be integrated into supplemental feeds such as pollen patties or dietary syrup for managed pollinators to reduce risk of organophosphate insecticides.

Herein is reported a biomaterial approach to control organophosphate toxicity aimed at managed bees (that is, bumblebees such as the common eastern bumblebee, *Bombus impatiens*, or the western honeybee, *Apis mellifera*) using OPT-loaded microparticles (FIG. 1). *B. impatiens* was used for the in vivo assays, although a similar gut pH exists for *A. mellifera*; thus, the results may be relevant to *A. mellifera* as well. Calcium carbonate microparticles were chosen to deliver OPT on the basis of several design considerations.

First, the microparticles mimic pollen grains in size and are therefore easily consumed by bees. Both bumblebees and honeybees have a gastrointestinal (GI) tract composed of a crop and ventriculus separated by a proventricular valve which mechanistically extracts micro-sized particles for digestion.

Second, by harnessing the acid scavenging capability of $CaCO_3$, the microparticles can protect OPT from unfavorable acidic GI conditions to maintain enzyme bioactivity once they are consumed by bees. The pH of the crop and ventriculus are 4.8 and 6.5, respectively, well below the optimal pH conditions of OPT.

Third, $CaCO_3$ microparticles (2-50 μm) are relatively easy and inexpensive to produce in large quantities and are capable of loading biomacromolecules during production. With optimized fabrication parameters and, importantly, the inclusion of gelatin as an additive, homogenously sized microparticles were produced that encapsulated OPT at ~90% efficiency and displayed a superior suspension stability in sucrose. In vitro studies confirmed the protective effect of the microparticles on OPT bioactivity. The OPT-encapsulated pollen-inspired microparticles (OPT-PIMs) allowed 100% survival of microcolonies of bees fed malathion-contaminated pollen patties, while 0% survival was observed for those fed with OPT alone or plain sucrose after 5 and 4 days, respectively.

To understand the protective properties and stability of PIMs, bees were fed PIMs loaded with a FITC-labelled protein, human serum albumin (HSA-PIMs). Fluorescent imaging confirmed almost complete extraction of PIMs out of the crop stomach by 1 hour and their stability throughout digestion for 12 hours. This versatile, scalable, low-cost detoxification strategy can act as a precautionary or remedial measure for managed pollinators when pollinating in areas of organophosphate application, to address the issue of pollinator exposures.

Methods

OPT synthesis. Ampicillin, chloramphenicol and IPTG solutions were sterilized before use. *E. coli* bearing pQE30-PTE was cultured in Miller grade LB broth containing 100 μg ml-1 ampicillin and 25 μg $ml^{-1}$ chloramphenicol at 37° C. Once cultures in 5,000 ml flasks reached optical density (OD) 0.4, 500 μl $CoCl_2$ (1 M) was added, and at OD 0.8-1.0, 500 μl IPTG (200 mg ml-1) was added for every liter of culture. The culture was left for a further 3 hours before collecting. The culture was then centrifuged for 10 min at 1,333×g in 11 centrifuge tubes, the supernatant was removed and the cell pellet was resuspended in 40 ml resuspension buffer (3.15 g Tris-HCl, 29.22 g NaCl, 56 g glycerol, 44 μl $CoCl_2$ (1 M), 144 mg imidazole, 1 l $H_2O$). The solution was then sonicated at 65% amplitude (5 s on, 25 s off) for 20 min in an ice bath. The solution was subsequently centrifuged for 1.5 hours at 4,333×g and the supernatant collected as crude OPT. Crude OPT was purified using a histidine-select NTA-nickel bead affinity column. The column was equilibrated using an equilibration buffer (20 mM phosphate buffer, 300 mM NaCl, 10 mM imidazole) before crude OPT was run through the column and washed with further equilibration buffer. Captured OPT was then eluted with elution buffer (20 mM phosphate buffer, 300 mM NaCl, 250 mM imidazole). OPT was concentrated using Amicon Ultra 15 ml 3-kDa-membrane tubes and washed with saline three times. OPT concentration was determined using a BCA protein assay kit. Confirmation of OPT production was confirmed using SDS-PAGE.

OPT-PIM fabrication. In a 10 ml vial, 1 ml of each of the following was added in order and mixed continuously for 10 s using a magnetic stirrer at 6,000 r.p.m.: 24 mg $ml^{-1}$ gelatin from porcine skin, OPT 3.364 mg $ml^{-1}$ (5% PFC) or OPT 1.345 mg $ml^{-1}$ (2% PFC), 0.33 M $CaCl_2$) and 0.33 M $Na_2CO_3$, to form OPT-PIMs. The solution was centrifuged at 1,000×g for 3 min and the supernatant subsequently removed. The remaining microparticles were suspended in either distilled water or 2 g $ml^{-1}$ sucrose to form 0.5 mg ml-1 OPT. The experiment was carried out ten times through these experiments.

Microparticle morphology. Microparticle morphology was analyzed by resuspending PIMs in 1 ml of distilled $H_2O$ following centrifugation and analyzing a drop of the solution under an EVOS FL microscope. To produce $CaCO_3$ microparticles to compare as a standard, the microparticle fabrication process was repeated without gelatin; distilled $H_2O$ was added in substitute. Lyophilized microparticles were furthered analyzed under SEM.

Results and Discussion

Figure 2A:
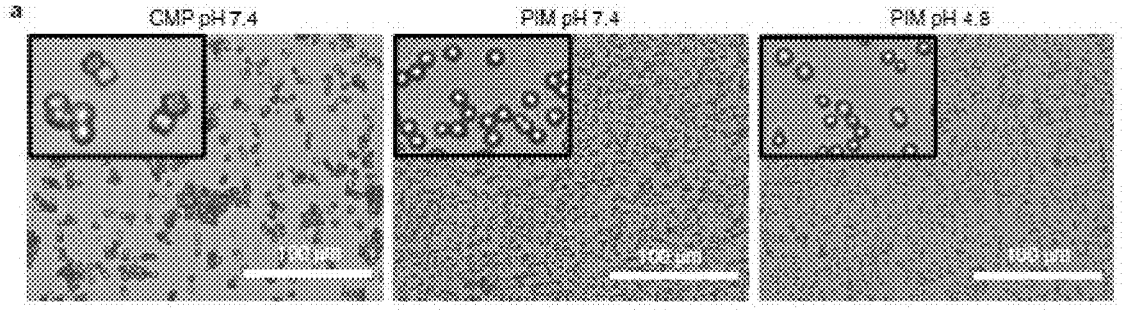
FIGS. 2A-2G. Characterizations and analysis of the stability, size distribution and morphology of PIMs.

Characterizations of PIMs. Calcium carbonate microparticles can be easily fabricated by rapidly mixing equimolar 0.33 M solutions of $CaCl_2$ and $Na_2CO_3$. Size and shape can be acutely controlled by altering synthesis parameters such as stirring speed, time and additive inclusion. Initially, $CaCO_3$ microparticles were fabricated with no inclusion of an additive, nor control of stirring time. The product displayed high incidences of aggregation, calcite crystal growth and poor size homogeneity (FIG. 2A); the average diameter was around 8.2±5.7 μm with a large size distribution under pH 7.4, which caused poor suspension stability.

Figures 2B, 2C:
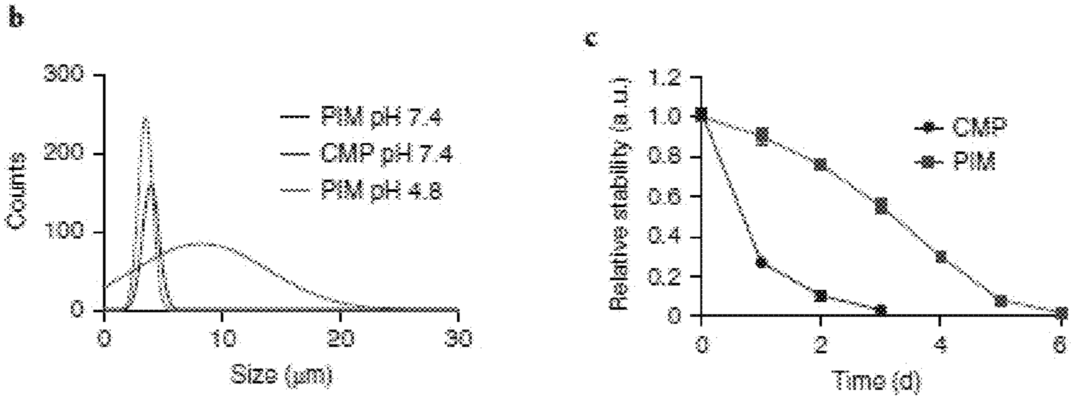

To circumvent these challenges, stirring time was restricted to 10 s and included gelatin (24 mg $ml^{-1}$) as an additive, which resulted in smaller and consistently homogenously sized (3.9±0.7 μm) microparticles. Gelatin was chosen because it is an easily obtained, low-cost natural additive. It is known that the zeta potential of gelatin is −13.2 mV (ref. 42.) and it could thus interact with $Ca^{2+}$ to form a gelatin-Ca complex that acts as a nucleation agent, subsequently enhancing microparticle stability. Given that these microparticles can be digested by bees in similar ways to pollen grains, the microparticles are herein also referred to as pollen-inspired microparticles or PIMs (FIG. 2B). PIMs displayed a superior suspension stability in sucrose.

Figures 2D, 2E:
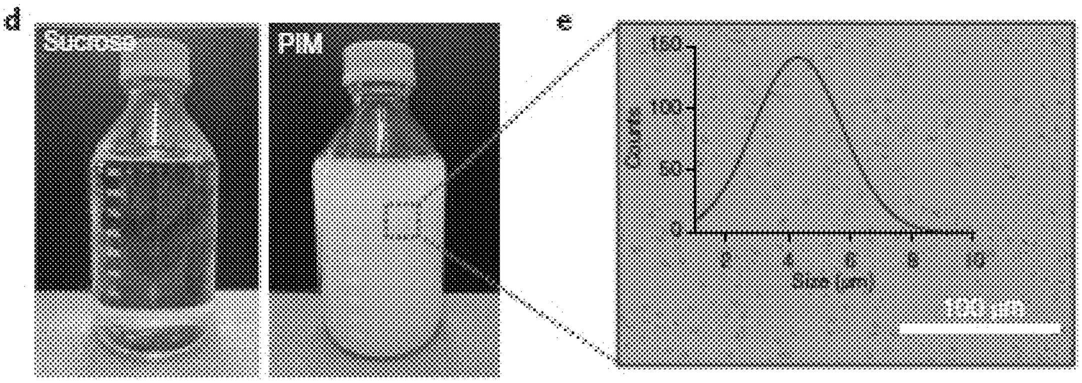
Figure 2F:
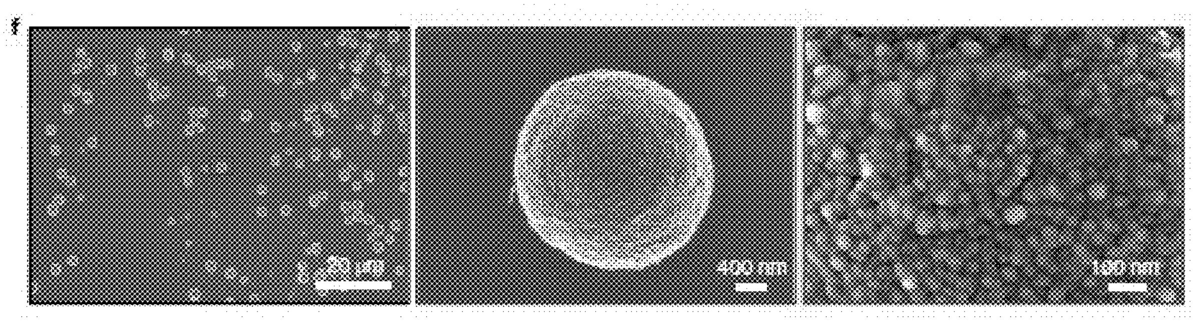

The significantly improved suspension stability was confirmed using a biophotometer that measured the uppermost layer of the microparticle suspension. After 2 days, ca. 90% of unmodified microparticles had settled while >75% of PIMs maintained good suspension stability. PIMs took 6 days to fully settle, whereas unmodified microparticles only took 3 d (FIG. 2C). The sucrose media used to suspend the microparticles was at a typical concentration used to feed wintering honeybees (2 g $ml^{-1}$). Although the molecular mechanism behind crystal growth and aggregation is unclear, scanning electron microscope (SEM) imaging confirmed that the gelatin-modified microparticles maintained a highly porous nanoparticle aggregation structure (FIG. 2F). Nanometer-size pores can provide accessible channels for biomacromolecule diffusion and a high internal surface area to allow physical adsorption with high substrate loading.

Figure 2G:
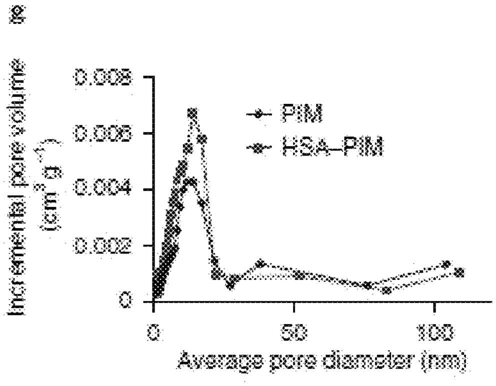

Since OPT-PIMs need to maintain function when passing through acidity presented by the crop stomach, the PIM stability was tested in pH 4.8 for 30 min PIMs at pH 4.8 displayed a fractional shift to a smaller size distribution (3.4±0.6 μm) (FIG. 2B). When the test was extended to 1.5 h, the PIMs still largely retained their shape, although the average particle size further decreased to 1.4±0.4 μm. The PIM fabrication process was then repeated using high reagent volumes to demonstrate the capacity for large-scale manufacture. PIMs were successfully produced at a 1 L total volume (FIG. 2D) and displayed a size distribution comparable to that of PIMs fabricated at small scale, with an average size of 4.3±1.4 μm (FIG. 2E). Microparticle pore size was analyzed in accordance with density functional theory using N2 adsorption isotherms. PIM nanochannel volumes dropped from 0.0067 to 0.0043 $cm^3$ $g^{-1}$ following HSA encapsulation, which further confirmed protein loading (FIG. 2G). Nanochannel diameters only dropped from 14 to 12 nm, which indicated that protein loading did not block channels and would still permit OPs to enter for enzymatic degradation.

Figure 3A:
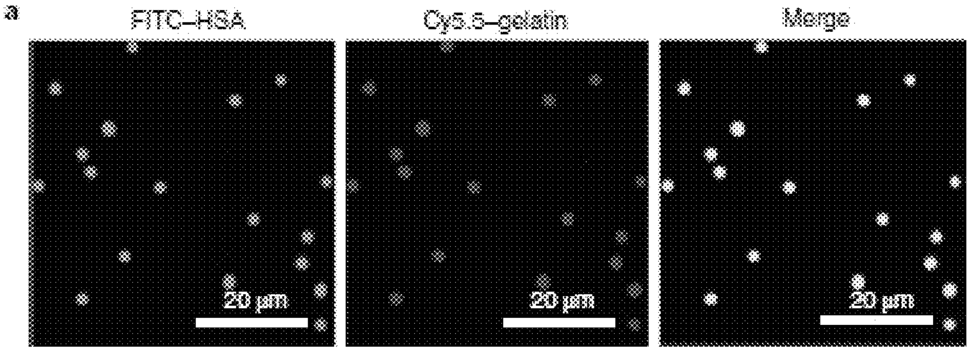
FIGS. 3A-3G. Characterizations of OPT encapsulation and activity in PIMs.
Figures 3B, 3C:
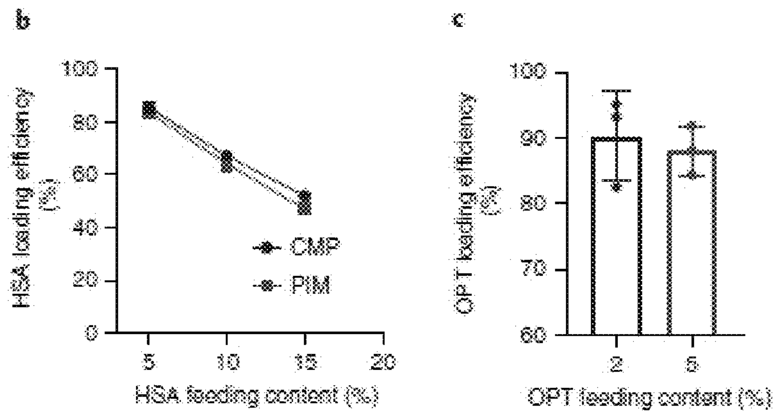

In vitro degradation of organophosphate pesticides with OPT-PIMs. Protein loading and gelatin modification of PIMs was further confirmed through confocal laser scanning microscopy. HSA was used in this instance as a model protein. Microparticles exhibited an overlay of Cy5.5-conjugated gelatin and FITC-conjugated HAS (FITC-HSA) in the full morphology of each microparticle (FIG. 3A). The confocal laser scanning microscopy (CLSM) imaging indicated gelatin conjugation and protein loading throughout the microparticle volume. The protein loading efficiency (PLE, percentage of protein loaded inside the microparticles relative to the total amount of protein added), as characterized spectrophotometrically using the FITC-HSA, varied as a function of the protein feeding content (PFC, percentage of the total amount of protein added relative to the total mass of the protein and microparticles). From the PLE and PFC, the protein loading capacity (PLC, the total entrapped amount of protein divided by the total mass of the protein-loaded microparticles) was also calculated. HSA-PIMs presented a high PLE of 85.5% (PLC=4.31%) for gelatin-modified PIMs and 83.6% (PLC=4.21%) for unmodified microparticles at 5% PFC (FIG. 3B). The loading efficiency decreased as the PFC increased. For PIMs, a PLE of 67.1% (PLC=6.94%) was obtained at 10% PFC, and a PLE of 52.1% (PLC=8.42%) was obtained at 15% PFC. In the case of unmodified microparticles, a PLE of 64.1% (PLC=6.65%) and a PLE of 47.1% (PLC=7.67%) were obtained, respectively (FIG. 3B).

Considering the loading efficiency decrease at higher PFCs and the intrinsic value of OPT, 5% was selected as a baseline to test OPT loading in PIMs. OPT presented 88.1% PLE (PLC=4.43%) at 5% PFC and 90.1% PLE (PLC=1.81%) at 2% PFC (FIG. 3C). It was herein found that a concentration of 0.5 mg $ml^{-1}$ OPT was sufficient to initiate rapid hydrolysis of methyl paraoxon to visibly form nitrophenol. A 2% PFC yielded an OPT concentration of 1.21 mg $ml^{-1}$ in OPT-PIMs, which could be further diluted to 0.5 mg $ml^{-1}$; this dilution offered adequate sucrose to render the solution sufficiently attractive to bumblebees for consumption. Furthermore, it was herein found that no protein was released from the PIMs up to 7 d following fabrication while suspended in 2 g $ml^{-1}$ sucrose.

It is known that OPT catalytic efficiency and conformational stability can vary on structural mutagenesis and variation in the central metal cation. In the present experiments, wild-type $Co^{2+}$-bound phosphotriesterase (molecular weight 39 kDa) was used, which is the optimum metalloenzyme complex capable of a $K_{cat}$ $K_m^{-1}$ of $7.6\times10^7$ $M^{-1}$ $s^{-1}$ in hydrolyzing paraoxon, where $K_{cat}$ is the turnover number and describes how many substrate molecules are transformed into products per unit time by a single enzyme, and $K_m$ gives a description of the affinity of the substrate to the active site of the enzyme.

Figures 3D, 3E:
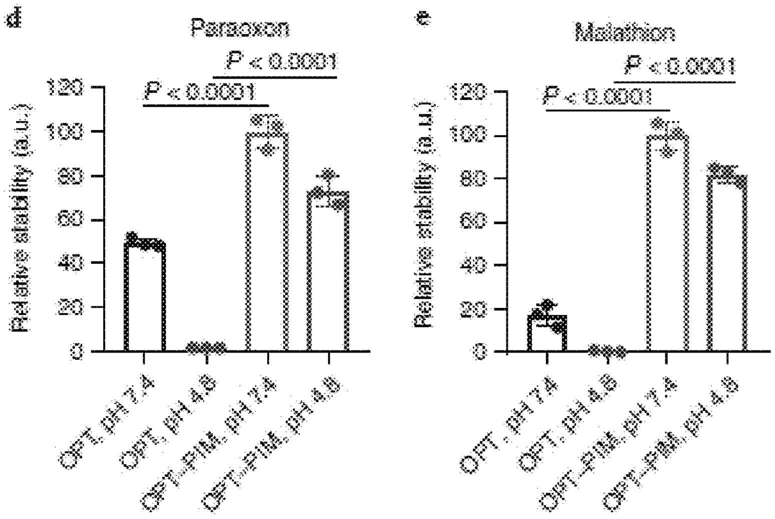

For the successful function of the design, it is critical that OPT-PIMs are able to maintain bioactivity in the conditions of a bee digestive tract (pH 4.8 in the crop stomach). Therefore, bioactivity and enzyme stability of OPT-PIMs and free OPT were assessed in vitro over a pH range using OPT 0.5 mg $ml^{-1}$ and either 0.5 mM paraoxon or 0.44 mM malathion. Paraoxon assays were carried out by measuring the absorbance of nitrophenol as it is produced from the OPT-catalyzed degradation of paraoxon. The relative enzymatic activity was obtained by normalizing the absorbances of both free OPT and OPT-PIMs to that of OPT-PIMs incubated at pH 7.4. As shown in FIG. 3D, free OPT yielded an activity of 49.7%, approximately half that of OPT-PIMs at pH 7.4. Meanwhile, the $K_m$ was determined to be 1.83 mM for OPT-PIMs, lower than that of free OPT (4.80 mM) in 2 g $ml^{-1}$ sucrose. The maximum velocity (Vmax) of OPT-PIMs (0.45 mM $min^{-1}$) was approximately three times that of free OPT (0.13 mM $min^{-1}$). Without being bound by theory, it is possible that the higher performance of OPT-PIMs occurs because microparticle encapsulation facilitates enhanced enzyme kinetics. In addition, the $CaCO_3$ element of the microparticle structure should possess an 'acid scavenging' ability, which could neutralize acid in the microparticle's immediate vicinity, thus allowing encapsulated OPT to outperform free enzyme in acidic conditions. OPT-PIMs at pH 4.8 displayed lower activity (73.4%) than that at pH 7.4. However, free enzyme assays almost did not function at all (1.7%) at pH 4.8.

An absorbance from malathion hydrolysis was characterized using Ellman's reagent (5,5'-dithiobis-2-nitrobenzoic acid or DTNB), which can react with the thiol group of malathion's breakdown product to form 2-nitro-5-thiobenzoate or $TNB^{2-}$, which has an absorbance at 412 nm. In malathion degradation assays, a similar trend could be detected at both pH 7.4 and pH 4.8. OPT is less adept at cleaving thiol groups, and therefore enzymatic degradation of malathion is relatively slow. Therefore, free OPT displayed a much lower activity of 17.1% at pH 7.4 and 0.6% at pH 4.8 (FIG. 3E). However, OPT-PIMs could still maintain high activity of 82.2% at pH 4.8. This indicates that the benefits of the microparticle design are more pronounced when degrading OPs because OPT can degrade relatively slowly. The superior catalytic performance of PIMs in pH 4.8 demonstrates the importance of utilizing a biomaterial element to protect enzyme catalysts in oral consumption.

Figures 3F, 3G:
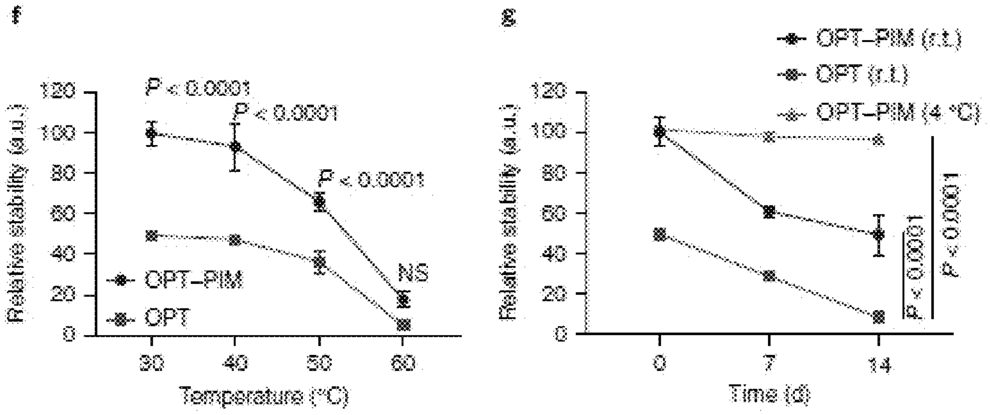

Further experiments were aimed at better understanding the stability of the detoxifying system under significant thermal stress, as any treatment could experience high summer temperatures when administered to bees. OPT has been found to denature at temperatures exceeding 45° C. Thus, experiments were conducted to determine whether microparticle encapsulation offers any protection from thermal denaturation. The capacity for the microparticle design to withstand elevated temperatures was tested by measuring paraoxon breakdown following enzyme incubation at temperatures ranging from 30 to 60° C. The relative enzymatic activity was obtained by normalizing the absorbances of both free OPT and OPT-PIMs to that of OPT-PIMs incubated under 30° C. As shown in FIG. 3F, free OPT displayed half the bioactivity of OPT-PIMs under 30° C. The enzymatic activity of free OPT dramatically dropped to 36.5% after incubation at 50° C., whereas the activity of OPT-PIMs remained at 66.3% at the same temperature. Further, increases in temperature>60° C. resulted in little catalytic activity (5.0%) of the free enzyme, which is much lower than that of OPT-PIMs (17.7%). It was herein found that OPT maintained greater bioactivity when encapsulated in PIMs relative to the case of free OPT as temperatures increased. The foregoing result is important for the potential application of the present design, as it has been shown capable of being administered at elevated temperatures.

To gauge the time taken for treatment to lose functionality, bioactivity of each group treatment relative to OPT-PIMs was measured over time when kept at room temperature (25° C.). Microparticle activity maintained around 60% of original activity after 7 days and 49.5% after 14 days, whereas free enzyme activity reduced to ~30% and <10%, respectively. OPT-PIMs stored at 4° C. maintained almost 100% activity after 14 d (FIG. 3G). The microparticle's capacity for long-term bioactivity and protein sequestration indicates a practical shelf life of the design. Other enzyme-engineering efforts, such as genetic engineering of the catalytic and binding pockets, introducing additional chemical functionalities, such as disulfide bridges or fluorine moieties, or incorporation of additives such as sugars, polyols, detergents, polymers and amino acids, may improve the catalytic efficiency of OPT and further enhance its storage stability.

Figures 4A, 4B:
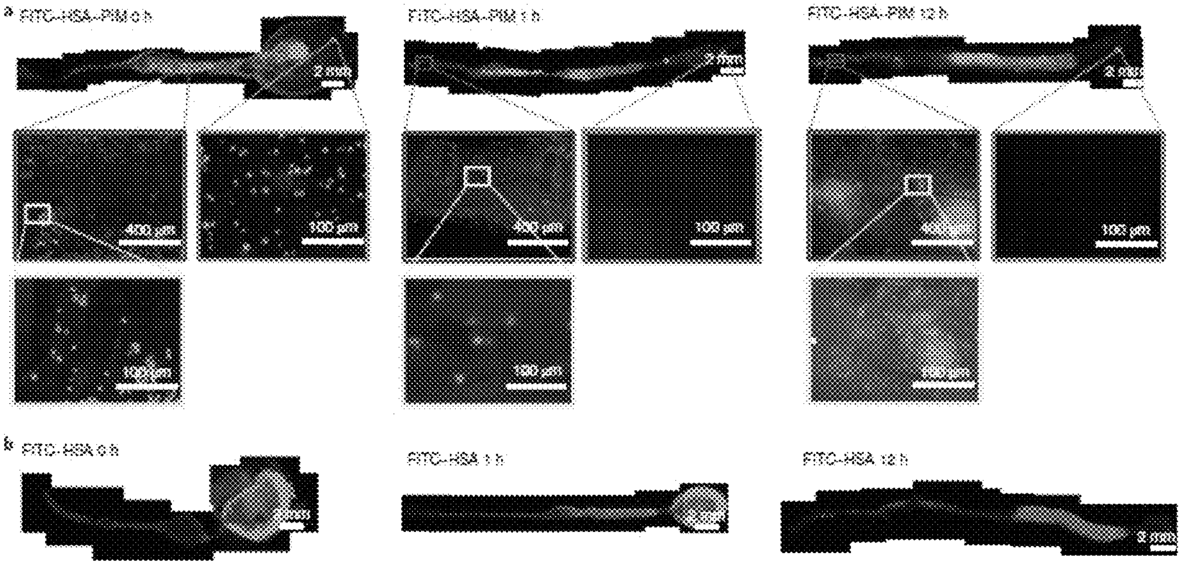
FIGS. 4A-4B. Tracking of digested PIMs by fluorescent imaging of bumblebee GI tracts.

In vivo characterizations of PIMs. *B. impatiens* were used for in vivo experimentation because colonies can be maintained indoors during the winter in a practical and accessible box. Bumblebees are known to display a susceptibility to OPs comparable to *A. mellifera*. To understand the retention performance of PIMs once consumed, bumblebees were fed microparticles loaded with FITC-labelled HSA (FITC-HSA-PIMs) and free FITC-HSA for 30 min, before extracting digestive tracts over a 12 hour period for fluorescent microscopy analysis (FIGS. 4A and 4B). FITC displayed PIMs successfully in the crop stomach and ventriculus sections of the GI tract for samples collected at 0, 1, 4 and 12 hours. During the first hour of digestion, microparticles were distributed across both the crop stomach and ventriculus. By 1 hour, the majority of microparticles had travelled out of the crop stomach, before clearance into the ventriculus, suggesting proventricular filtering of PIMs (FIG. 4A). By 12 hours, no PIMs were observable in the crop stomach, comparable to background autofluorescence of untreated bee, but a significant number of PIMs were still detected in the posterior section of the GI tract. In case of free FITC-HSA, most of the fluorescence was located in the ventriculus at 4 hours, while a large amount was observed in crop stomach at 1 hour (FIG. 4B). The data suggest that PIMs are digested akin to pollen grains, thus increasing the number of microparticles drawn into the ventriculus alongside pollen. This maximizes PIM function in detoxifying pollen as it is digested. This is significant because OPs are often found in high quantities in pollen, which may be held in the posterior section of the ventriculus for digestion for up to 12 h or more. The degree of fluorescence was not able to be quantified because FITC fluorescence is pH dependent; the presence of microparticles would have altered stomach pH to the point where fluorescence readings would have been inaccurate. However, these images qualitatively suggest that the PIM design improved retention and provided protection from the denaturation of loaded proteins.

Figure 5A:
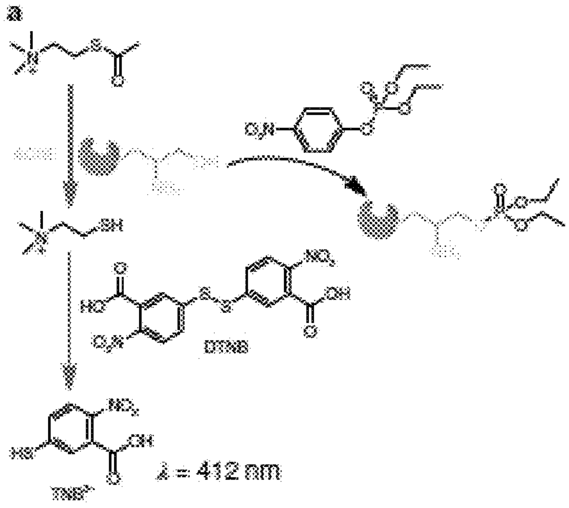
FIGS. 5A-5F. Characterization of OPT-PIM efficacy through AChE activity assay and bee survival experiments.
Figure 5B:
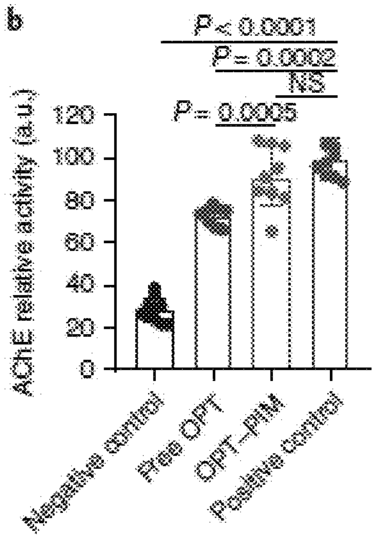

Efficacy and survival studies. The characterization of OPT-PIM efficacy was further validated via quantification of AChE activity when mixed with the above described treatment and paraoxon. As AChE is inhibited by OPs such as paraoxon, high AChE activity would indicate effective detoxification through the above described treatment. Acetylthiocholine cleavage via AChE can be used to quantify AChE activity, as the thiocholine product reacts with DTNB to form $TNB^{2-}$, which has an absorbance at 412 nm (FIG. 5A). Homogenized honeybee cells were able to maintain 91.5% of AChE activity when treated with 0.5 mM paraoxon and OPT-PIMs, relative to the positive control (homogenized honeybee cells without any paraoxon treatment). This was a stark improvement in AChE functionality relative to the negative control (homogenized honeybee cells treated with paraoxon but no free OPT or OPT-PIMs treatment), which resulted in a relative activity reduction of ~72%. Samples treated with free OPT retained 18.8% less activity than that of samples treated with OPT-PIMs (FIG. 5B).

Figure 5C:
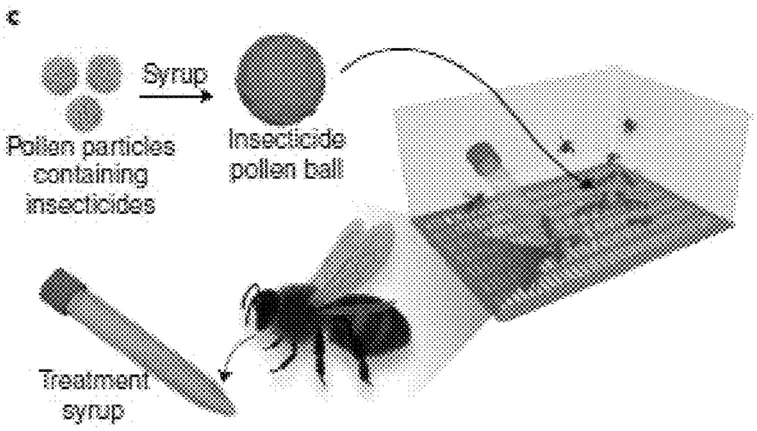
Figures 5D, 5E, 5F:
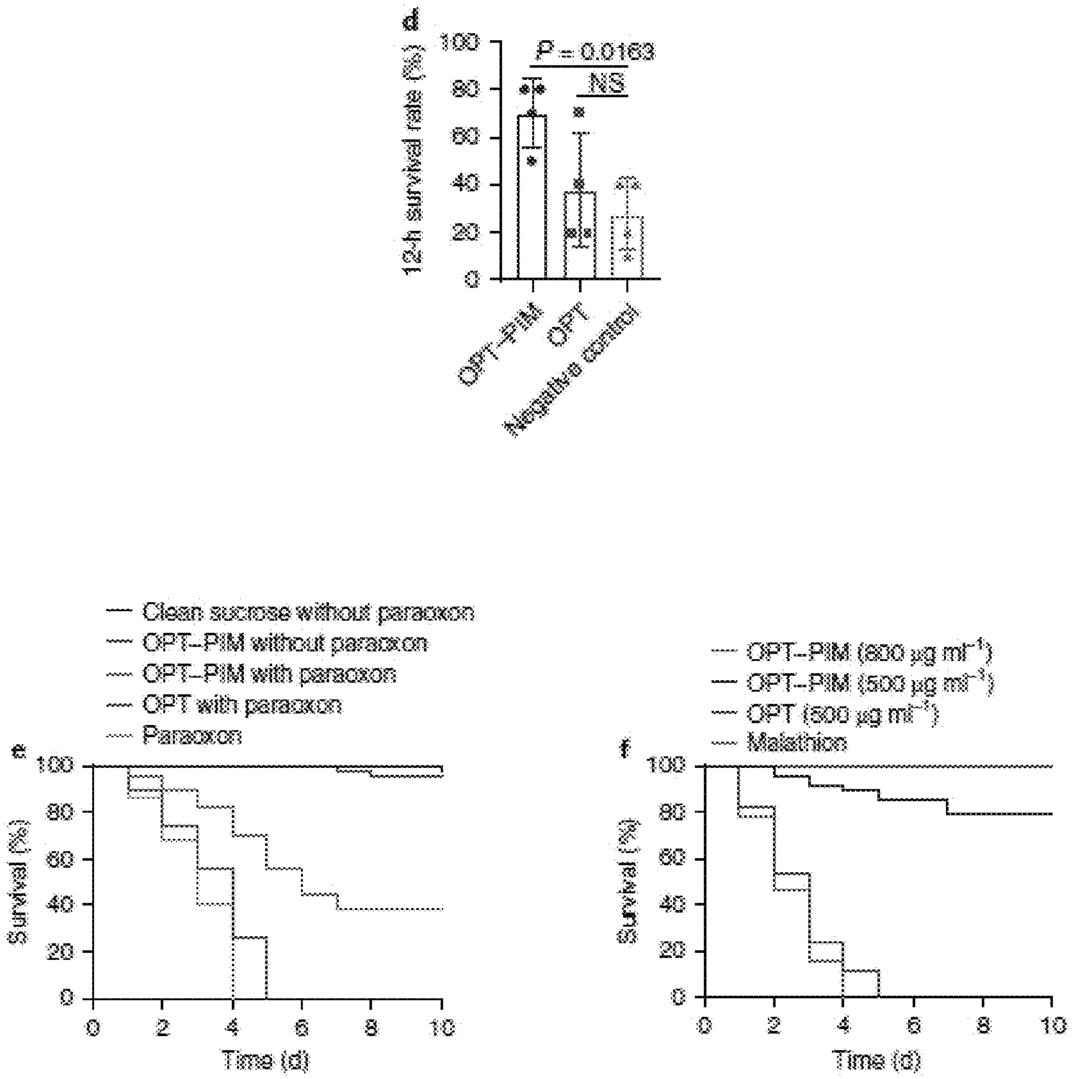

Groups of 50 bumblebees were treated with paraoxon or malathion-contaminated pollen balls and OPT-sucrose treatments to determine the efficacy of treatments in reducing mortality under OP exposure (FIG. 5C). Paraoxon and malathion present oral $LD_{50}$s for honeybees at 0.0175 and 0.38 μg per bee, respectively. This data set a benchmark for OP doses for administration and subsequent detoxification to demonstrate OPT-PIM efficacy. Bumblebees consume approximately 40.5 μg pollen per day depending on body mass. Based on this figure, pollen balls were initially formed containing 0.432 μg $g^{-1}$ paraoxon and 9.383 μg $g^{-1}$ malathion to feed without enzyme treatment as a negative control. It was herein found that these pollen balls caused no health deterioration after one week. Subsequently, through trial and error, the contamination was significantly increased to concentrations that caused significant mortality. Pollen balls were tested containing 50 μg $g^{-1}$ paraoxon over 12 hours to measure the OPT-PIM impact against acute exposure. In this trial, OPT-PIMs at 500 μg $ml^{-1}$ of OPT were able to maintain a 70% survival rate, whereas free enzyme- and sucrose-treated groups sustained 62.5 and 72.5% fatalities, respectively (FIG. 5D). Although OPT-PIMs largely detoxified acute exposure, the catalytic efficiency was not able to fully mitigate mortality.

A moderate level of toxicity was tested using 15 μg $g^{-1}$ paraoxon and 750 μg $g^{-1}$ malathion-contaminated pollen balls against 50 μg $ml^{-1}$ OPT treatments. Free OPT and no treatment resulted in 100% mortality after 5 and 4 days, respectively, following paraoxon toxicity. OPT-PIMs were able to maintain a slower incidence of mortality relative to other treatments. After 10 days, 38% of the group sample had survived. Groups containing non-contaminated pollen balls and either pure sucrose or PIM-sucrose maintained 100% and 96% survival, respectively. A minor level of mortality is generally typical in any sample after 10 days (FIG. 5E). In malathion contaminated samples, OPT-PIM at 800 μg $ml^{-1}$ of OPT was able to maintain 100% survival for the duration of observation, a lower concentration of 500 μg $ml^{-1}$ maintained above 80% survival over 10 days. Free OPT and sucrose-treated groups presented 100% mortality after 5 and 4 days, respectively, analogous to the paraoxon trial (FIG. 5F). Without being bound by theory, the poor performance of free, unprotected OPT may be in part driven by its higher denaturation in the acidic conditions of the digestive tract. Pollen grains are known to release their internal contents as they progress along the midgut. It may be assumed that any OPs absorbed into pollen grains during incubation are also made available at this stage of digestion. This means that for the effective detoxification of contaminated pollen, OPT must retain bioactivity until it makes passage into the ventriculus. In addition, it is critical that a high concentration of OPT is drawn into the midgut to intercept paraoxon or malathion as pollen is digested. Both of these conditions have been facilitated via OPT encapsulation in PIMs.

CONCLUSIONS

Experimentation has shown that PIMs are able to enhance the bioactivity of OPT. OPT-PIMs outperform free OPT when tested under unfavorable conditions of temperature, storage and pH. The microparticle design described herein rendered OPT suitable for use in pollinator OP intoxication, as it bestows functionality in gastric acidity and can maintain performance for longer durations under elevated thermal stress. The microparticle design has also improved the functionality of OPT during digestion by considering the bee's digestive system. Microparticles are extracted into the midgut and retained for a long duration. The aforementioned advantages ultimately result in a lower rate of mortality when treated with OPT-PIM relative to free OPT. The benefits are most appreciable when degrading OPs, which are typically hydrolyzed at a lower relative rate, as in the case of malathion. This work has produced a viable product to mitigate insecticide damage to pollinator colonies and revealed new ways in which research can address the impacts of insecticide application through improving this current design, or by exploring new microparticle treatments.

While there have been shown and described what are at present considered the preferred embodiments of the invention, those skilled in the art may make various changes and modifications which remain within the scope of the invention defined by the appended claims.

What is claimed is:

1. A composition comprising microparticles wherein each microparticle comprises:

(i) a phosphotriesterase;

(ii) nanoparticles; and (iii) a surface active agent;

wherein the microparticles have a core-shell arrangement in which the shell surrounds the core, wherein the core comprises the phosphotriesterase, the shell comprises the nanoparticles, and the surface active agent is in the core, the shell, or both.

2. The composition of claim 1, wherein the nanoparticles are inorganic nanoparticles.

3. The composition of claim 2, wherein said inorganic nanoparticles have a carbonate composition.

4. The composition of claim 3, wherein said carbonate composition is a calcium carbonate or magnesium carbonate composition.

5. The composition of claim 1, wherein said nanoparticles have an acid-scavenging composition.

6. The composition of claim 1, wherein the nanoparticles have a size in a range of 1-500 nm.

7. The composition of claim 1, wherein the surface active agent is a polymer.

8. The composition of claim 1, wherein the surface active agent is gelatin.

9. The composition of claim 1, wherein the phosphotriesterase and the surface active agent are dispersed throughout each microparticle.

10. The composition of claim 1, wherein said phosphotriesterase is dissolved or suspended in an aqueous medium within each microparticle.

11. The composition of claim 10, wherein said aqueous medium has an alkaline pH.

12. The composition of claim 1, wherein said microparticles have a size in a range of 0.1-100 microns.

13. The composition of claim 1, wherein said microparticles have a size in a range of 1-100 microns.

14. The composition of claim 1, wherein said microparticles possess an outer surface porosity characterized by pores having a pore size in a range of 1-500 nm.

15. The composition of claim 1, wherein said microparticles possess an outer surface porosity characterized by pores having a pore size in a range of 1-100 nm.

16. An aqueous suspension comprising microparticles of any one of claims 1-15 suspended in an external aqueous medium.

17. The aqueous suspension of claim 16, wherein said suspension contains an insect pollinator attractant.

18. The aqueous suspension of claim 17, wherein said insect pollinator attractant is sucrose.

19. The aqueous suspension of claim 18, wherein said sucrose is present in a concentration of 1-5 g/mL in said external aqueous medium.

20. A method of detoxifying insect pollinators from one or more organophosphate pesticides, the method comprising placing a detoxifying aqueous suspension in a location accessible to the insect pollinators to permit the insect pollinators to ingest the detoxifying aqueous suspension, wherein said detoxifying aqueous suspension comprises microparticles suspended in an external aqueous medium containing an insect pollinator attractant, wherein each microparticle comprises:

(i) a phosphotriesterase;

(ii) nanoparticles; and (iii) a surface active agent;

wherein the microparticles have a core-shell arrangement in which the shell surrounds the core, wherein the core comprises the phosphotriesterase, the shell comprises the nanoparticles, and the surface active agent is in the core, the shell, or both.

21. The method of claim 20, wherein said organophosphate pesticide is selected from one or more of the group consisting of malathion, parathion, methyl parathion, chlorpyrifos, diazinon, dichlorvos, phosmet, fenitrothion, tetrachlorvinphos, azamethiphos, azinphos-methyl, azinphos-ethyl, and terbufos.

22. The method of claim 20, wherein said insect pollinators comprise the order Hymenoptera.

23. The method of claim 20, wherein said insect pollinator attractant is sucrose.

24. The method of claim 20, wherein said method results in at least 50% survival of the insect pollinators compared to insect pollinators administered said external aqueous medium without said microparticles.

25. The method of claim 20, wherein the nanoparticles are inorganic nanoparticles.

26. The method of claim 20, wherein said nanoparticles have an acid-scavenging composition.

27. The method of claim 20, wherein the surface active agent is a polymer.

28. The method of claim 20, wherein the surface active agent is gelatin.

29. The method of claim 20, wherein the phosphotriesterase and surface active agent are dispersed throughout each microparticle.

30. The method of claim 20, wherein said phosphotriesterase is dissolved or suspended in an aqueous medium within each microparticle.

31. The method of claim 30, wherein said aqueous medium has an alkaline pH.

32. The method of claim 20, wherein the microparticles have a size in a range of 0.1-100 microns.

33. The method of claim 20, wherein the microparticles have a size in a range of 1-100 microns.

34. The method of claim 20, wherein said microparticles possess an outer surface porosity characterized by pores having a pore size in a range of 1-500 nm.

35. The method of claim 20, wherein said microparticles possess an outer surface porosity characterized by pores having a pore size in a range of 1-100 nm.

36. The composition of claim 1, further comprising pollen admixed with the microparticles.

37. The composition of claim 1, further comprising an insect pollinator attractant.

38. The composition of claim 1, further comprising one or more nutrients for insect pollinators.

39. The composition of claim 38, wherein the one or more nutrients are selected from one or more carbohydrates, amino acids, vitamins, minerals, or lipids.

* * * * *